(12) United States Patent
Mittelstein et al.

(10) Patent No.: US 6,820,490 B2
(45) Date of Patent: Nov. 23, 2004

(54) SYSTEMS AND METHODS FOR MEASURING PRESSURE

(75) Inventors: Michael Mittelstein, Laguna Niguel, CA (US); John T. Sorensen, Ladera Ranch, CA (US); James B. Gerg, Lake Forest, CA (US); Soheila Mirhashemi, Laguna Niguel, CA (US)

(73) Assignee: Neomedix Corporation, San Juan Capistrano, CA (US)

( * ) Notice: Subject to any disclaimer, the term of this patent is extended or adjusted under 35 U.S.C. 154(b) by 0 days.

(21) Appl. No.: 10/273,379

(22) Filed: Oct. 16, 2002

(65) Prior Publication Data

US 2003/0115965 A1 Jun. 26, 2003

Related U.S. Application Data

(60) Provisional application No. 60/330,172, filed on Oct. 16, 2001.

(51) Int. Cl.[7] ............................................... G01L 7/08
(52) U.S. Cl. ......................................... 73/715; 73/700
(58) Field of Search ................................... 73/700–756

(56) References Cited

U.S. PATENT DOCUMENTS

| | | | | |
|---|---|---|---|---|
| 5,614,677 A | * | 3/1997 | Wamsiedler et al. | ........ 700/186 |
| 5,753,820 A | * | 5/1998 | Reed et al. | .................... 73/706 |
| 5,955,659 A | * | 9/1999 | Gupta et al. | ................ 73/54.01 |
| 6,164,313 A | * | 12/2000 | Walters | ....................... 137/218 |
| 6,171,253 B1 | * | 1/2001 | Bullister et al. | ............ 600/486 |

FOREIGN PATENT DOCUMENTS

| | | | | | |
|---|---|---|---|---|---|
| JP | | 62135652 A | * | 6/1987 | .......... F02M/23/04 |
| JP | | 06158696 A | * | 6/1994 | ........... E03C/1/298 |

* cited by examiner

*Primary Examiner*—Edward Lefkowitz
*Assistant Examiner*—Jermaine Jenkins
(74) *Attorney, Agent, or Firm*—Robert D. Buyan; Stout, Uxa, Buyan & Mullins, LLP

(57) ABSTRACT

Methods and systems for measuring the pressure of a fluid. A flexible barrier separates the fluid from the pressure receiving surface of a pressure sensing device. The pressure of the fluid is transferred through the flexible barrier to the pressure receiving surface. The flexible barrier may be in abutting juxtaposition with or may be spaced apart from the pressure sensing surface. In either case, the flexible barrier is coupled or held in defined relationship to the pressure sensing surface such that the pressure receiving surface will receive the substantially actual pressure of the fluid even when the pressure of the fluid is less than the ambient atmospheric pressure. Coupling of the flexible barrier to the pressure receiving surface may be achieved by any suitable means, including adhesive or the application of a full or partial vacuum between the flexible barrier and the pressure receiving surface.

14 Claims, 4 Drawing Sheets

SYSTEMS AND METHODS FOR MEASURING PRESSURE

RELATED APPLICATION

This patent application claims priority to U.S. Provisional Patent Application Ser. No. 60/330,172 filed on Oct. 16, 2001, the entirety of which is expressly incorporated herein by reference.

FIELD OF THE INVENTION

The present invention relates to devices and methods for sensing pressure, and more particularly to vacuum-coupled and gas-volume-coupled pressure sensing systems and their methods of use.

BACKGROUND OF THE INVENTION

Pressure measurements are attained by determining the magnitude of a force that is applied to a unit area. A pressure sensor is a device that reads changes in the force applied to the unit area and transmits indicia of such changes in force to another apparatus. The transmitted indicia of changes in force may be converted to an electrical, mechanical, or pneumatic parameter and may provide a display or reading of the pressure.

Pressure sensors may use various means for sensing and transmitting indicia of force per unit area. Some common types of pressure sensors include simple fluid-filled columns to pistons, deflecting members, strain gauges, semiconductor piezoresistive apparatus, piezoelectric sensors (including dynamic & quasistatic measurement types), microelectromechanical systems (MEMS), vibrating elements, optical pressure sensors and variable capacitance systems. Depending on the type of pressure sensor employed, the indicia of changes in force per the unit area my be transmitted from the pressure receiving pressure sensor to a pressure transducer in various forms, including the transmission of pressure waves through a fluid-filled column, transmission of electromagnetic signals through a wire or wireless connection or transmission of optical signals through optical fibers.

In some instances it is desirable to disallow direct contact between the fluid or other matter in which pressure is to be sensed and some pressure receiving surface(s) of the pressure sensor, transducer or other apparatus in the system. For example, in cases where one desires to measure changes in the pressure of a sterile fluid being pumped through a pump housing or conduit, it will likely be desirable to avoid direct contact between that sterile fluid whose pressure is being measured and any non-sterile components of a pressure sensor and/or transducer. Similarly, in cases where it is desired to measure the pressure of a corrosive or potentially damaging fluid (e.g., an acid) being pumped or fed through a pipeline it may be desirable to avoid direct contact between that fluid and any metal or other surfaces within the pressure sensor or transducer that my become corroded or damaged by the corrosive or otherwise damaging fluid. Or, in cases where it is desired to measure the pressure of blood flowing through an artery or vein of a human or veterinary patient, it is clearly desirable to avoid direct contact between the patient's blood and any non-sterile or potentially toxic components of the pressure sensor or transducer.

Accordingly, there is a need for the development of barriers for a) preventing direct contact between the fluid or other matter in which the pressure is to be sensed and the pressure receiving surfaces of the pressure sensor, transducer or other apparatus used for obtaining the desired pressure measurement while, at the same time, b) allowing accurate transmission of the pressure changes or other indicia of changes in force per unit area to be transmitted to the pressure receiving surfaces of the pressure sensor, transducer or other apparatus without undue damping, distortion or disruption. Although placement of an interposed flexible film or membrane may serve to prevent direct contact between the fluid or other matter in which the pressure is being measured and the pressure receiving surfaces of the pressure sensor, transducer or other apparatus, the use of such flexible film or membrane may be problematic in systems where the pressure(s) being sensed is/are at least some of the time negative or below ambient, as the presence of such negative or sub-ambient pressure on one side of the film or membrane may tend to pull the film or membrane away from the pressure sensing surface, thereby interfering with or preventing accurate measurement of the negative or sub-ambient pressure.

As those of skill in the art will recognize, certain medical procedures are performed in which fluid irrigation and aspiration loops are superimposed upon a generally enclosed surgical sight for the purposes of maintaining visibility and/or removing tissue and/or debris from the surgical field. For example, for ophthalmic procedures in the eye, irrigation flow and inflation of the eye is often achieved by allowing an irrigation fluid (e.g., basic salt solution) to undergo gravity flow from an elevated bottle or bag containing the irrigation fluid, through tubing lines to the eye. An aspiration apparatus such as a peristaltic pump or other aspiration type pump may be used to aspirate the aspirant from the eye through another tube. It is often desirable to accurately determine the pressure of the aspirant fluid within the housing of the aspiration pump or in the tube that runs from the eye to the aspiration pump. However, especially when the pressure is measured within the pump, such pressure may at least some of the time be negative (e.g., less than the ambient atmospheric pressure). Thus, the pressure sensor used in such application must be capable of sensing negative (as well as positive) pressure. Furthermore, it is desirable for the irrigation solution to be sterile and free of contaminants. Thus, if the pressure sensing device contains a non-sterile or contaminated pressure receiving surface, it will be desirable to prevent the aspirant from coming in direct contact with the pressure receiving surface of the pressure sensor.

SUMMARY OF THE INVENTION

The present invention overcomes at least some of the shortcomings of the prior art by providing pressure measuring devices and methods wherein flexible barriers prevent direct contact between the fluid or other matter in which the pressure is being measured and the pressure receiving surfaces of the pressure sensing devices (e.g., transducers, pressure switches, pistons, deflecting members, strain gauges, semiconductor piezoresistive apparatus, piezoelectric sensors (including dynamic & quasistatic measurement types), microelectromechanical systems (MEMS), vibrating elements (silicon resonance, for example), optical pressure sensors, variable capacitance systems or other pressure measuring apparatus). One example of a particular pressure sensing apparatus that may be used in at least some embodiments of the invention is that commercially available under the name SenSym Type 19c from InvEnsys Sensor Systems, Milpitas, Calif. The flexible barriers are coupled to the pressure receiving surfaces of the sensing apparatus such that the pressure exerted against the flexible barrier is transmitted to and accurately received by the pressure sensing apparatus even in situations where the pressure exerted against the flexible barrier is negative as would tend to pull or separate the flexible barrier from the pressure sensing apparatus. This coupling of the flexible barrier to the pressure sensing apparatus may be accomplished by various means including the creation of a vacuum between the flexible barrier and the pressure sensing apparatus, the application of an adhesive between the flexible barrier and the pressure sensing apparatus, the capturing of a fixed volume of fluid (e.g, liquid or suitable) between the flexible barrier and the pressure sensing apparatus or the exclusion of all or all but a small amount of air from the space between the flexible barrier and the pressure sensing apparatus and the sealing of such space to prevent subsequent inflow of fluid between the flexible barrier and the pressure sensing apparatus. Thus, the pressure sensors of this invention are useable to measure negative or sub-ambient as well as positive fluid pressure.

Further in accordance with the invention, in at least some embodiments and particularly in those in embodiments where the pressure sensing system is being used to obtain dynamic pressure measurements (e.g., continuous pressure monitoring, monitoring of a pressure waveform or tracing and/or rapidly sensing changes in pressure), it is desirable to minimize the compliance of all components of the system including the flexible barrier member and any gas, liquid, adhesive material or other matter interposed between the flexible barrier and the pressure sensing apparatus. Accordingly, in some embodiments of this invention, the material and construction of the flexible barrier and the means by which the flexible barrier is coupled to the pressure receiving surface of the pressure sensing apparatus may be made as non-compliant as possible, thereby avoiding possible damping or attenuation of the pressure measurement due to excessive system compliance. In this regard, those embodiments in which the flexible membrane is affixed directly to and is maintained in abutting and continuous contact with the pressure receiving surface of the pressure sensing apparatus (e.g., where the flexible barrier is coupled to the pressure sensing apparatus by vacuum or thin layer of adhesive) will likely be of relatively minimal compliance and may be better suited to applications wherein the system is used for such dynamic pressure monitoring. Other embodiments wherein the flexible barrier is more compliant, or where some fluid-filled or compressible-matter-containing space exists between the flexible barrier and the pressure sensing apparatus may be of higher compliance and may be more suited to static pressure monitoring or applications where in rapid or instantaneous pressure measurements are not required (e.g., measuring process pressures that do not change rapidly, measuring mean pressure, etc.

Further in accordance with this invention, some of the pressure sensing systems provided comprise a disposable portion and a reusable portion, wherein the flexible barrier member prevents direct contact between the reusable portion (which may be contaminated or potentially toxic/damaging to the fluid) and the fluid in which pressure is being measured. Thus, such pressure sensing devices are useable in applications such as medical pumping devices, etc. wherein it is desired to measure the pressure of a fluid that is sterile or which otherwise would be damaged or changed if it were to come into direct contact with the pressure receiving surface(s) of the pressure sensing apparatus.

These general aspects of the invention, as well as numerous other aspects and advantages of the invention, will become apparent to persons of skill in the art who read and understand the following detailed description and the accompanying drawings.

DETAILED DESCRIPTION OF EMBODIMENTS OF THE INVENTION

The following detailed description and the accompanying drawings are provided for the purpose of describing and showing certain, but not all, embodiments or examples of the invention only and shall not be construed to limit the scope of the claims invention in any way.

Figure 1A:
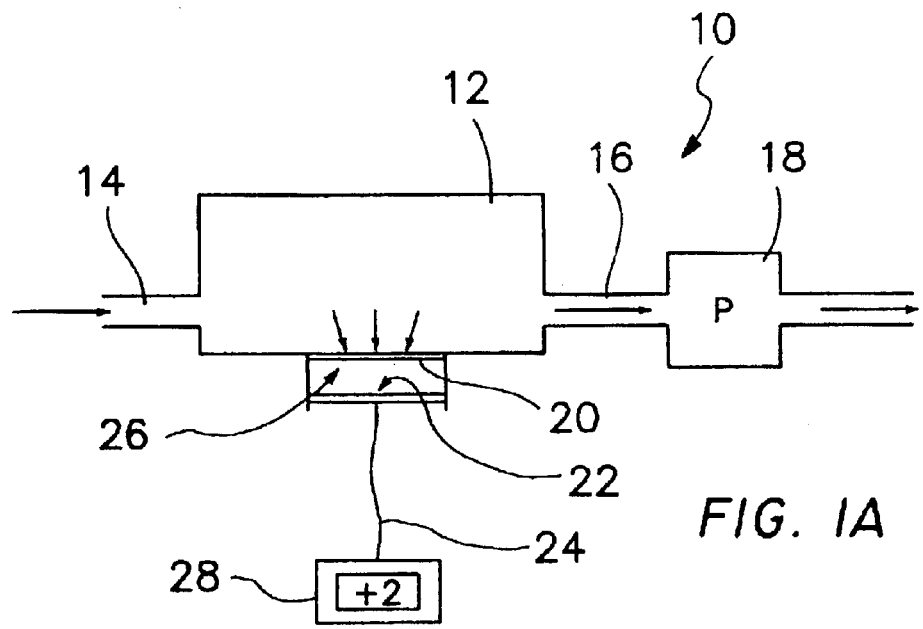
FIG. 1A is a schematic diagram of a pressure measuring system and method of the present invention while measuring a fluid that is under positive pressure.
Figure 1B:
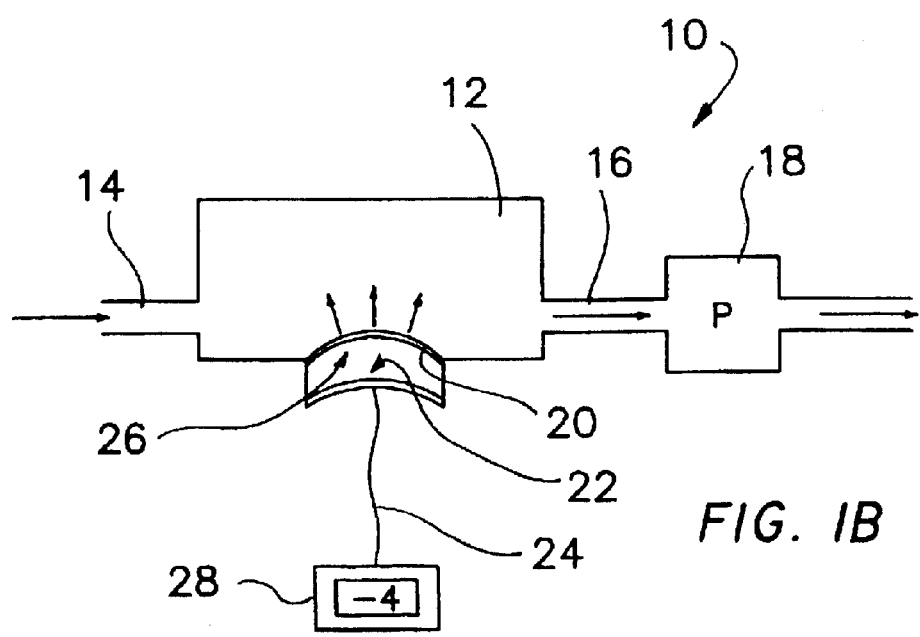
FIG. 1B is a schematic diagram of a pressure measuring system and method of the present invention while measuring a fluid that is under negative pressure.

FIGS. 1A and 1B show, in general schematic fashion, a system and method of the present invention, with FIG. 1A showing a situation where the system is measuring a fluid that is under positive pressure and FIG. 1B showing the same system while measuring a fluid that is under negative (i.e., less than ambient atmospheric) pressure. As shown, the system generally comprises a chamber 12 having a fluid inlet 14 through which a fluid may pass into the chamber 12 and a fluid outlet 16 through which the fluid exits the chamber 12. The inlet side of a pump 18 is attached to the fluid outlet 16 so as to aspirate fluid through the inlet 14, through the chamber 12 and through the outlet 16. It is to be appreciated, however, that the above-described pump 18 and fluid conduits and/or other specific structural aspects of this example are provided solely for purposes of enhancing understanding of the invention and illustrating one example of a particular application in which the pressure sensing systems of this invention will be useable. The embodiments below are not described in conjunction with such pump 18, conduits or lines so that the broad applicability of this invention may be appreciated. Indeed, the pressure sensing systems of this invention may be used in a wide variety of applications not limited to aspirated of pumped fluid streams.

In FIG. 1A, the pressure and flow through inlet 14 is sufficient to maintain the slightly positive fluid pressure within the chamber 12. However, in FIG. 1B the pressure and/or flow of fluid through inlet 14 has become diminished or blocked while the pump 18 continues to aspirate, thereby causing the pressure of the fluid within the chamber 12 to be negative. In accordance with this invention, a pressure sensing apparatus is attached to the chamber 12 for measuring the pressure of the fluid within the chamber 12. This pressure sensing apparatus comprises a pressure sensor having a pressure receiving surface 22, such as a thin metal structure. The pressure sensor is connected by a signal transmission apparatus 24 (e.g., a wire, optical fiber, wireless connection, etc.) to a pressure display device 28 or any other means for providing the obtained information regarding the pressure. Changes in the pressure everted by the fluid within the chamber 12 on the pressure receiving surface 22 cause the pressure sensor to emit corresponding pressure signals. Those signals are transmitted though signal transmission apparatus 24 to present such pressure signal to for example to pressure signal processing apparatus (e.g., programable controller, microprocessor, etc.) and/or display (e.g., digital readout, needle gage, oscilloscope, etc.) 28. Where a display is used, such display may then convert the pressure signals into measured pressure value(s) (e.g., pounds per square inch, grams per cubic centimeter, torr, etc.) or a tracing or waveform and may display such value (s), tracing or waveform to the operator. In cases where a processing apparatus is used, such processing apparatus may process the pressure signals and issue corresponding control signals to control or vary the operation of another apparatus (e.g., to control the speed of a pump being used to aspirate fluid from the chamber). A flexible barrier 20 is disposed between the pressure receiving surface 22 and the fluid within the chamber 12, thereby preventing the fluid from coming in direct contact with the pressure receiving surface. A coupling zone 26 is definable between the pressure receiving surface 22 and the flexible barrier 20. In some embodiments, the flexible barrier may be in direct abutting contact (e.g., abutting juxtaposition) such that the coupling zone 26 has a width of zero and is virtually non-existent as there is essentially no space between the flexible barrier 20 and the pressure receiving surface 22. In those embodiments, a vacuum (e.g., negative pressure) may be created between the flexible barrier 20 and the pressure receiving surface 22 so as to hold the flexible barrier 20 and pressure receiving surface 20 in contact with one another even when, as shown in FIG. 1B, the pressure of the fluid within the chamber 12 becomes negative. In this manner, upward as well as downwardly directed force against the flexible barrier 20 will result in equal upwardly or downwardly directed force on the pressure receiving surface 22 without the need for direct contact between the fluid and the pressure receiving surface 22. In order to achieve this in situations where the pressure of fluid within the chamber 12 is negative, the vacuum (i.e., negative pressure) between the flexible barrier 20 and the pressure receiving surface 22 must be equal to or preferably more negative (i.e. greater negative pressure) than the most negative pressure that will be reached by the fluid within the chamber 12. Such embodiments embodiments wherein the flexible barrier 20 is maintained in direct and continuous contact with pressure receiving surface 22 of the pressure sensing apparatus will be of inherently low compliance and will be well suited for use in applications wherein dynamic pressure measurements are required (e.g., continuous pressure monitoring, monitoring of a pressure waveform or tracing and/or rapidly sensing changes in pressure) or where the pressure being monitored is subject to rapid variation.

In other embodiments, adhesive may be present within the coupling zone 26 to hold the flexible barrier 20 and pressure receiving surface 22 in abutting or fixed-distance, spaced-apart relationship to one another such that the exertion of downward or upward force by the fluid on the flexible barrier 20 will result in the exertion of substantially equivalent amounts of downward or upward force on the pressure receiving surface. In such embodiments, the peel strength of the adhesive may serve to hold the flexible barrier 20 and pressure receiving surface 22 in contact with one another as the vacuum had done in the above-described vacuum embodiment. As explained in more detail herebelow, in such embodiments where the flexible barrier 20 is spaced apart from the pressure sensing surface 22 of the pressure sensing apparatus, it will be desirable to ensure that the compliance of the system is sufficiently low to permit the system to be used in its intended application. Accordingly, if the coupling zone 26 is relatively small, the flexible barrier if formed of material and constructed in a manner to be of minimal compliance and the fluid, adhesive or other matter within the coupling zone is rigid or relatively non-compliant, the system may have sufficiently low overall compliance to permit it to be used for the more dynamic types of pressure measurements (e.g., continuous pressure monitoring, monitoring of a pressure waveform or tracing and/or rapidly sensing changes in pressure) whereas in embodiments where the flexible barrier has more inherent flexibility, elasticity or compliance and/or where the coupling zone is large and/or where the coupling zone contains captured air, larger amounts of compressible matter, compliant adhesive, etc.

In other embodiments, a fixed volume of gas (e.g., air) may be trapped within the coupling zone 26 to accomplish the desired coupling of the flexible barrier 20 to the pressure receiving surface 22.

In other embodiments, the coupling zone 26 may be sealed such that air can neither enter nor escape from the coupling zone 26, thereby substantially holding the flexible barrier 20 in fixed abutting or spaced-apart relationship to the pressure receiving surface.

Figure 2:
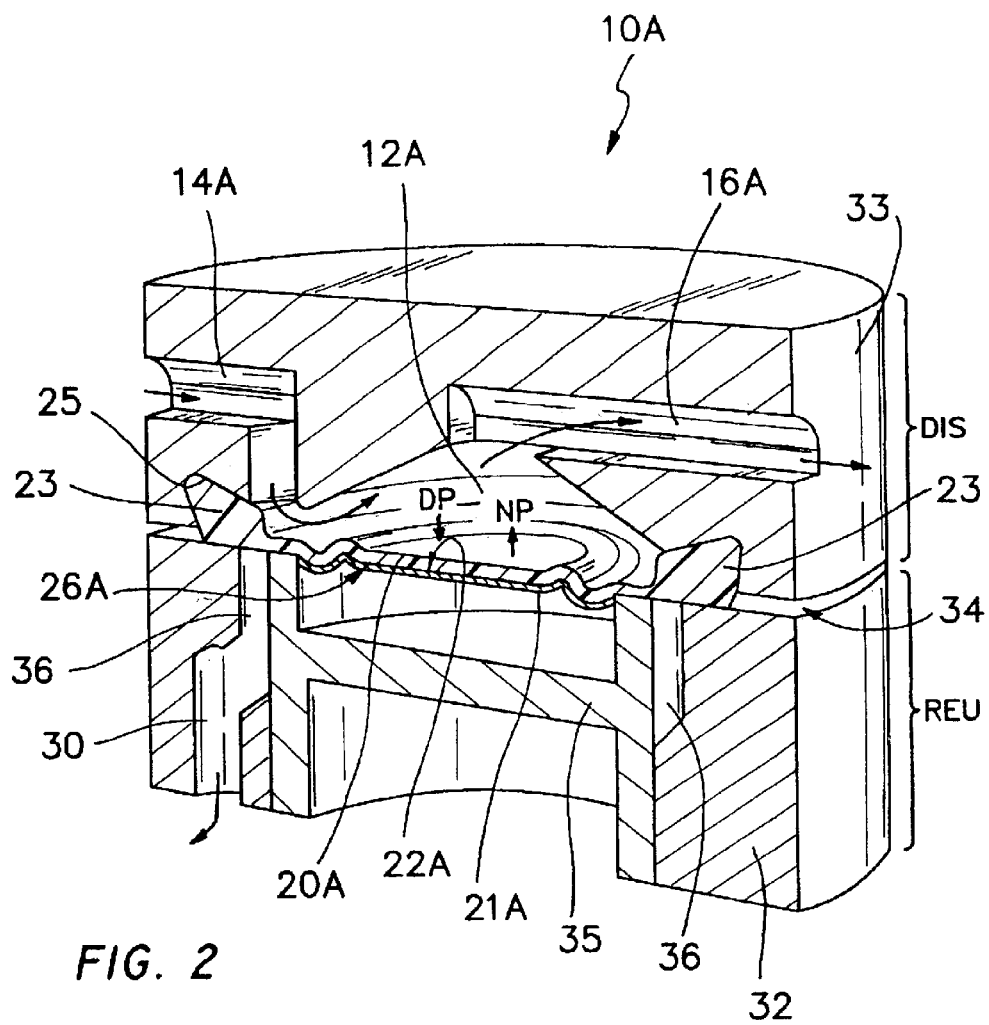
FIG. 2 is a sectional view of an embodiment of a pressure measuring system of the present invention wherein the flexible barrier is vacuum-coupled to the pressure sensing surface.
Figure 3A:
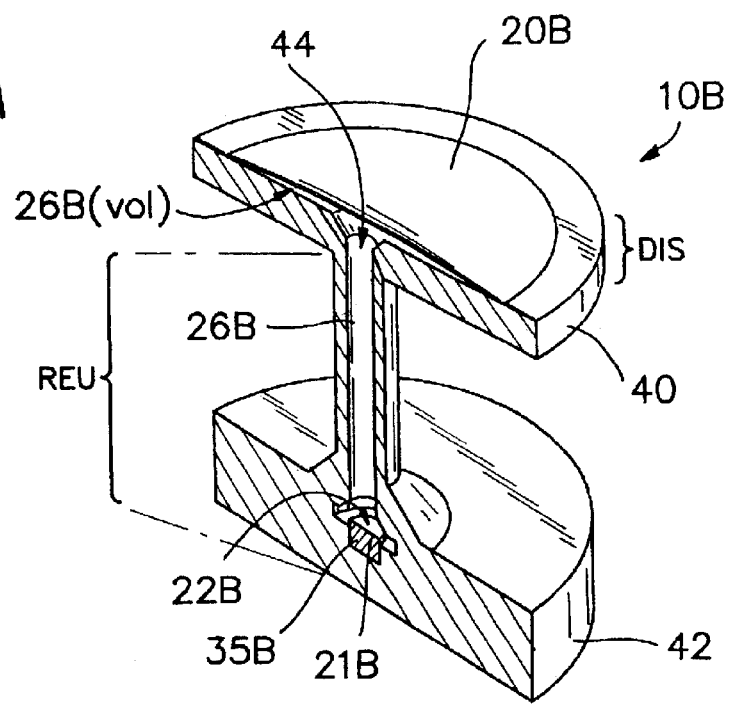
FIG. 3A is a sectional view of another embodiment of a pressure measuring system of the present invention wherein the flexible barrier is air-volume-coupled to the pressure receiving surface and while measuring a fluid that is at ambient atmospheric pressure.
Figure 3B:
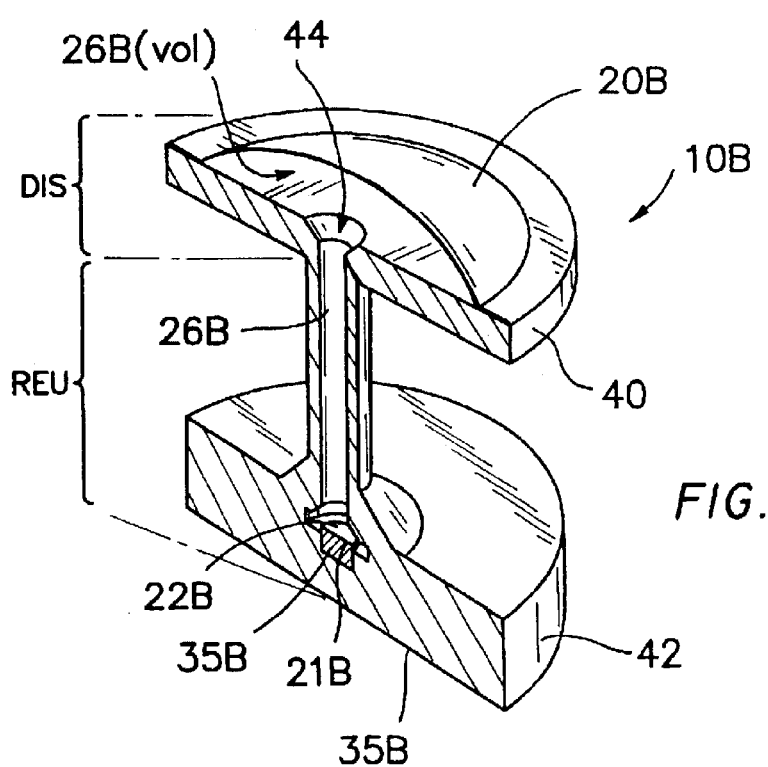
FIG. 3B is a view of the system of FIG. 3A while measuring a fluid that is at negative pressure.
Figure 4:
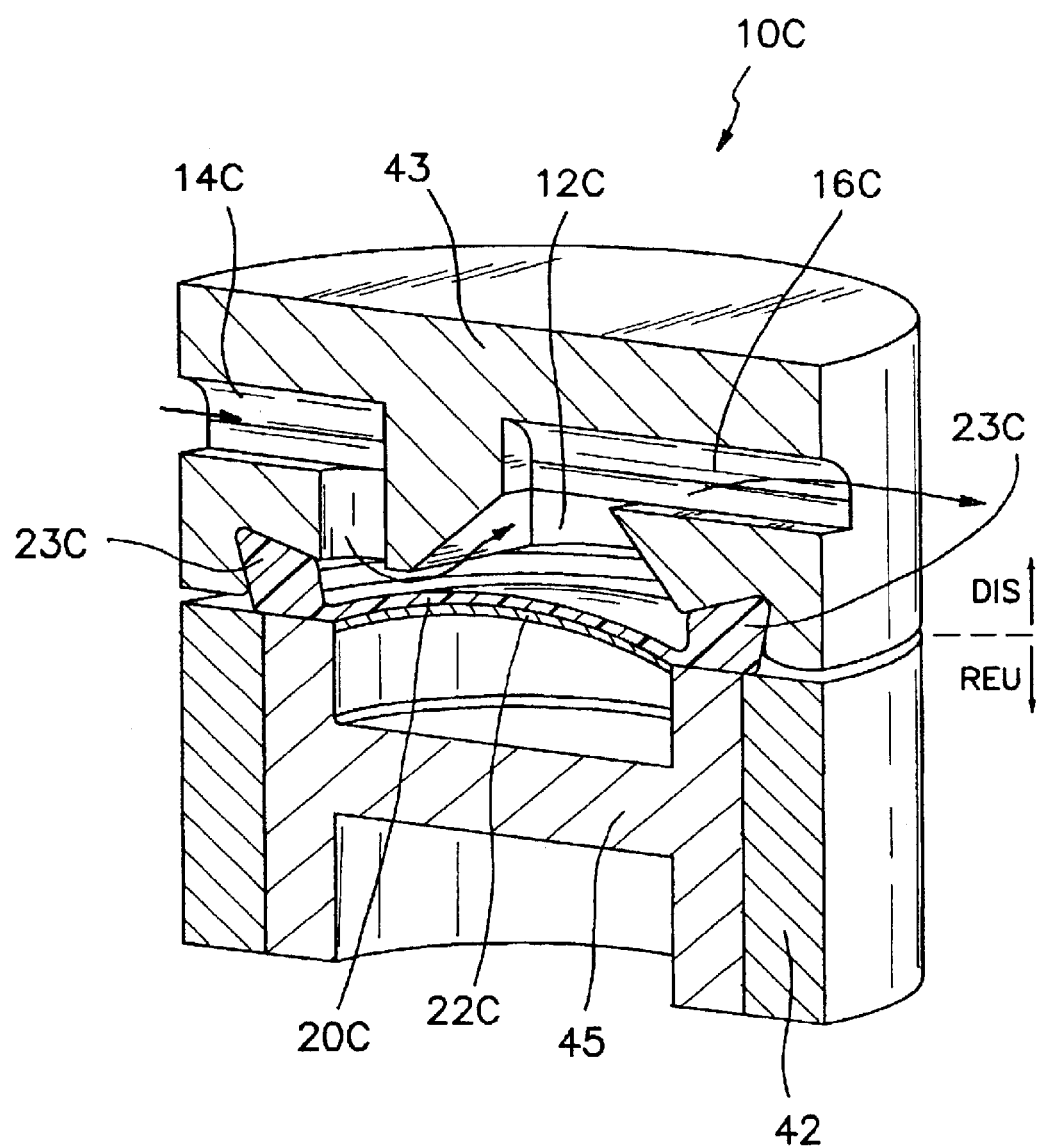
FIG. 4 is a sectional view of an embodiment of a pressure measuring system of the present invention wherein the flexible barrier is in substantial contact with the pressure sensing surface such that all or substantially all of the air is purged from the coupling zone and the coupling zone is sealed to prevent air from subsequently leaking into the coupling zone.

Several specific examples of pressure sensing systems, incorporating these alternative modes of coupling the flexible barrier 20 to the pressure sensing surface 22 are shown in FIGS. 2–4 and are described herebelow.

A. Vacuum-Coupled Membrane Pressure Sensor System

FIG. 2 shows an example of a pressure sensing system 10a of this invention wherein the flexible barrier 20a is vacuum-coupled to the pressure sensing surface 22a. This embodiment of the system 10a comprises a disposable assembly portion DIS and a reusable assembly portion REU. The disposable assembly portion comprises an upper housing 33 which has a fluid chamber 12a, fluid inlet 14a and fluid outlet 16a defined therewithin and a flexible barrier 20a mounted on the underside of the housing 12a, below the fluid chamber 12a. The flexible barrier has an enlarged periphery 23. The reusable portion comprises a lower housing 32 which has a pressure sensing apparatus 35 mounted therewithin and a vacuum channel 30 which extends through a portion of the lower housing 32 and coupled to a ring channel 36, facilitating evacuation of the coupling zone 26. In this regard, it is desirable in such embodiments for the pressure sensing apparatus to be in a vacuum-tight sealed relationship to the surrounding housing 32 so as to maintain the desired vacuum within the coupling zone 26. The pressure sensing apparatus 35 comprises a diaphragm 21 having an upper pressure receiving surface 22a. Changes in the force applied to the diaphragm's pressure receiving surface 22a cause the pressure sensor 35 to transmit pressure signals corresponding to the magnitude and direction of such changes in force, to a pressure display apparatus (not shown) or controller. The pressure display apparatus may convert such pressure signals into wave form(s) and/or pressure value(s) and may display such wave form(s) and/or pressure value(s) to the operator. Alternatively or additionally, a controller receiving such pressure signals may perform computations using such pressure signals or may utilize such pressure signals as the basis for triggering an alarm when the pressure is too high or too low and/or to control process variables or apparatus (e.g., to speed up, slow down or stop a pump that is aspirating fluid out of the outlet 16a).

In operation, the disposable assembly portion DIS is brought together with the reusable assembly portion REU, in the manner shown in FIG. 2, and vacuum (i.e., negative pressure) is applied to the vacuum channel 30 and ring channel 36, thereby evacuating air from the coupling zone 26 between the pressure receiving surface 22a of the diaphragm 21a and the adjacent flexible barrier member 20a. The amount of negative pressure applied to the vacuum channel 30 is preferably greater (i.e., more negative) than the greatest (i.e., most negative) pressure that will be exerted by the fluid within the fluid chamber 12a. The enlarged periphery 23 of the flexible barrier member 20a is sealed within a corresponding groove 25 formed in the underside of the upper housing 33 and may be firmly sealed within such groove 25 by adhesive or other suitable means. However, the use of adhesive or other sealant may be unnecessary in systems such as that shown in FIG. 2 wherein the groove 25 is tapered or wedge shaped such that the periphery 23 of the flexible barrier member 20a will be captured in sealing fashion within that grove 25. The underside of the peripheral portion 23 seats firmly against the upper surface of the lower housing 32 and is held firmly in place by the formation of the vacuum between the pressure receiving surface 22a and the flexible barrier 20a. In this manner the periphery 23 of the flexible barrier 20a acts as a seal, preventing leakage of air from space 34 into the evacuated region between the pressure receiving surface 22a and the flexible barrier.

When the pressure of fluid within the chamber 12a is positive, force will be directed in the downward direction against the flexible barrier 20a, as indicated by arrow PP on FIG. 2. When the pressure of fluid within the chamber 12a is negative, such fluid will tend to pull upwardly on the flexible barrier 20a as indicated by arrow NP of FIG. 2. However, so long as the negative pressure between the pressure receiving surface 22a and the flexible barrier member 20a is greater (i.e., more negative) than that of the fluid within the chamber 12a, the diaphragm 21a will remain in contact with the flexible barrier 20a and the pressure sensor 35 will accurately measure the negative pressure of the fluid within the chamber 12a.

B. Adhesive-Coupled Membrane Pressure Sensor System

Figure 2A:
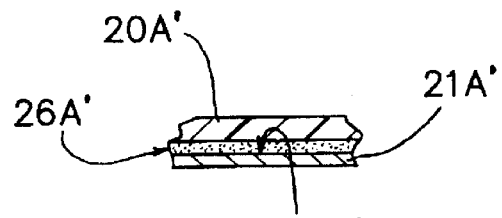
FIG. 2A is sectional view of a portion of the pressure measuring system of FIG. 2 modified such that the flexible barrier is coupled to the pressure receiving surface by adhesive rather than by vacuum-coupling.

As shown in FIG. 2a, in an adhesive-coupled variation of the pressure sensing system shown in FIG. 2 may be used. In this adhesive-coupled system 10a', a quantity of adhesive is disposed within the coupling zone 26a' to adhere the flexible barrier 20a' to the pressure receiving surface 22a' of the diaphragm 21a'. Thus, adhesive is used in addition to, or as an alternative to, the applied vacuum as the means for coupling the diaphragm 21a' to the flexible barrier 20a'. In embodiments where adhesive is used without vacuum, the system 10a' need not include the vacuum channel, but may otherwise be configured and constructed as shown in FIG. 2.

The adhesive may be pre-applied to the flexible barrier 20a such that upon assembly a temporary connection is created between the underside of the flexible barrier 20a' and the pressure receiving surface 22a' of the diaphragm 21a'. Consequently the flexible barrier 20a' will transfer not only positive fluid pressure but also negative fluid pressure (more specifically the suction or the partial vacuum of fluid within the chamber 12a) from the fluid to the sensing apparatus 35 as long as the adhesive coupling is stronger than the negative pressure of the fluid within the chamber 12a. Furthermore, in many applications it will be preferable to utilize a type of adhesive that will allow the adhesive connection to be broken without causing damage to or leaving residue on the diaphragm 21a or in any way damaging the reusable portion REU of the system 10a'.

C. Air Volume-Coupled Pressure Sensor System

FIGS. 3a and 3b show another example of a pressure sensing system 10b of this invention wherein the pressure receiving surface 22b of a pressure sensing member or diaphragm 21b is coupled to a flexible barrier member 20b by way of a coupling zone 26b wherein a fixed volume of air or other gas is contained.

This system 10b comprises a reusable assembly portion REU and a disposable assembly portion DIS. The reusable portion REU comprises a housing 42 having a pressure sensing device 35b which includes a sensor member or diaphragm 21b. The disposable portion DIS comprises a rigid platform member 40 having a flexible barrier member 20b mounted thereon such that the periphery of the flexible barrier member 20b is attached in sealed abutment with the rigid platform member 40. A coupling zone 26b which comprises an air filled chamber or passageway extends from the rigid platform 40 and opens through an aperture 44 into the coupling space 26b (vol) between the underside of the central portion of the flexible barrier 20b and the upper surface of the rigid platform member 40. The disposable portion DIS is attachable to the reusable portion REU such that a continuous, sealed coupling zone 26b extends from the underside of the central portion of the flexible barrier 20b to the pressure receiving surface 22b of the pressure sensing diaphragm 21b.

FIG. 3a shows the system 10b in a situation where a fluid under positive or near atmospheric pressure is adjacent the upper side of the flexible barrier member 20b while FIG. 3b shows the system 10b in a situation where a fluid under negative (i.e., sub-atmospheric) pressure is adjacent the upper side of the flexible barrier member 20b. The pressure sensing apparatus 35b is preferably a type having low compliance and ideally low internal "dead volume." The flexible barrier member 20b is preferably a membrane formed of a polymeric material which is substantially impermeable to air or whatever gas is trapped within the coupling zone 26b, 26b (vol). In this embodiment it is desired to minimize the volume of air (or other suitable gas) that is trapped within the coupling zone when the reuseable portion REU is sealed to the disposable portion DIS. While the volume of air or gas within that coupling zone 26b is mostly dictated by geometric considerations, the minimization of the volume from the coupling zone 26b (vol) between the upper surface of the rigid platform 40 and the undersurface of the flexible barrier member 20b is accomplished by allowing the barrier member 20b to be collapse as shown in FIG. 3a wile the reuseable and disposable portions REU, DIS are connected to one another. In this manner, the positive or negative pressure of fluid adjacent the upper side of the flexible barrier member 20b is transmitted through the barrier member 20b, though the air or gas trapped within the coupling zone 25b, 26b (vol) and to the pressure receiving surface 22b of the pressure sensing member or diaphragm 21b. In this embodiment as well as any other embodiment of the invention wherein a volume of air is trapped within the coupling zone 26b, the following relationships apply at a constant temperature:

$$PV = Constant = P_{initial}V_{initial} = P_{operational}V_{operational}$$

This implies that:

$$V_{operational} = V_{initial}P_{initial}/P_{operational}$$

For example, to measure a fluid pressure of ½ atmosphere absolute;

$$V_{operational} = (1.0/0.5)(V_{initial}) = 2.0\ V_{initial}$$

Likewise for the compliance associated to the air inside the system, the following relationships apply at a constant temperature:

Compliance=$C_{operational} = dV_{operational}/dP_{operational} = V_{initial}/P_{operational}$ where $V_{initial}$ is the air volume at atmospheric pressure. Note the inverse operational pressure dependence that increases compliance as pressure is reduced, for example at ½ atmosphere absolute the compliance is twice the compliance at atmospheric pressure.

Thus, in this particular example, as the barrier member 20b transitions from its initial collapsed or relaxed configuration shown in FIG. 3a to its fully distended configuration shown in FIG. 3b, it would preferably accommodate a volume of air filling the coupling zone 26a and 26a(vol) that is approximately equal to twice the initial trapped air volume within the coupling zone 26a, 26a (vol) without substantially stretching the preformed barrier member 20b, in order for the pressure sensor 35b to provide accurate readings of the negative fluid pressure adjacent the upper surface of the barrier member 20b. In other embodiments, this factor may be larger than 2× and could possibly be as high as 10×.

Likewise, it would be optimal, to minimize air volume $V_{initial}$ to insure that the preformed (inelastic) barrier member 20b is in a collapsed (minimum retained volume) configuration upon initializing the system. Thus, it may be desirable in at least some embodiments for the system 10b to include a retaining member or retainer (not shown) that would hold the barrier member in its collapsed (FIG. 3a) configuration until after the disposable portion DIS and reusable portion REU have been soundly attached and sealed to one another thereby creating a sealed coupling zone 26b, 26b (vol) between the underside of the barrier member 20b and the pressure receiving surface 22b of the sensor element or diaphragm 21b.

D. Sealed/Coupled Pressure Sensor System

FIG. 4 shows yet another example of a pressure sensing system 10 of this invention. This embodiment of the system comprises a disposable portion DIS which includes; a first housing 43 having a fluid chamber 12a, fluid inlet 14c and fluid outlet 16c formed therein and a flexible barrier member 20c having an enlarged peripheral region 23c and a reusable portion REU which includes; a second housing 42 and a pressure sensing apparatus 45 mounted within the housing 42, such pressure sensing apparatus 45 comprising a pressure receiving member or diaphragm 21c and a pressure receiving surface 22c on that diaphragm 21c. In this embodiment of the system 10c, the components are constructed such that as the disposable portion DIS is attached to the reusable portion REU, all or nearly all air is forced out from between the underside of the flexible barrier member 20c and the upper pressure receiving surface 22c of the pressure sensing member or diaphragm 21c. The configuration of the pressure receiving surface 22c (e.g., a convex surface as shown in FIG. 4) may facilitate the purging of air from the area between the flexible barrier 20c and the pressure receiving surface 22c as the system is assembled. The enlarged peripheral portion 23c of the barrier member 20c forms a seal which prevents air from leaking or being drawn into the region between the barrier member 20c and pressure sensing diaphragm 22c, even when the fluid pressure adjacent the upper surface of the barrier member 20c is negative as would tens to pull the barrier membrane away from the pressure sensing diaphragm 22c. In this manner the barrier member 20c and pressure sensing diaphragm 22c are maintained in direct contact with one another without the need for the application of vacuum or adhesive as in the embodiment shown in FIGS. 2 and 2a. Here the seal is formed by the periphery 23c of the barrier member 22c being captured and compressed between the housings 42, 42 in such a way that almost all air is expelled during the process of connection the disposable portion DIS to the reusable portion REU, as may be done by any suitable means including but not limited to threaded engagement, bayonet connection, magnetic connection, etc.

Although exemplary embodiments of the invention have been shown and described, many changes, modifications and substitutions may be made by those having ordinary skill in the art without necessarily departing from the spirit and scope of this invention. For example, elements, components or attributes of one embodiment or example may be combined with or may replace elements, components or attributes of another embodiment or example to whatever extent is possible without causing the embodiment or example so modified to become unuseable for its intended purpose. Accordingly, it is intended that all such additions, deletions, modifications and variations be included within the scope of the following claims.

What is claimed is:

1. A system for measuring the pressure of a fluid, said system comprising:

a pressure sensing apparatus having a pressure receiving surface and components for transmitting indicia of the pressure exerted against the pressure receiving surface;

a flexible barrier disposed between the pressure receiving surface and the fluid, said barrier being coupled to the pressure receiving surface such that accurate sensing of the fluid pressure will occur even if the pressure of the fluid is or becomes less than the ambient atmospheric pressure; and a vacuum channel through which negative pressure may be applied to evacuating air from between the flexible barrier and the pressure receiving surface.

2. A system according to claim 1 wherein the flexible barrier comprises a polymer membrane.

3. A system according to claim 1 wherein the flexible barrier is in abutting juxtaposition with the pressure receiving surface.

4. A system according to claim 3 wherein the flexible barrier remains in abutting juxtaposition with the pressure receiving surface even when the pressure of the fluid is less than the ambient atmospheric pressure.

5. A system according to claim 4 wherein the flexible barrier is coupled to the pressure receiving surface such that the space between the flexible barrier and the pressure receiving surface remains substantially the same even when the pressure of the fluid is below ambient atmospheric pressure.

6. A system according to claim 1 wherein the flexible barrier is spaced apart from the pressure receiving surface.

7. A system according to claim 1 wherein the flexible barrier is coupled to the pressure receiving surface by adhesive.

8. A system according to claim 1 wherein the flexible barrier is coupled to the pressure receiving surface by at least a partial vacuum between the flexible barrier and the pressure receiving surface, said vacuum being sufficient to cause the space if any, between the flexible barrier and the pressure receiving surface to remain substantially constant even when the pressure of the fluid is less than the ambient atmospheric pressure.

9. A system according to claim 1 wherein direct contact between the fluid and the pressure sensing surface would result in undesired contamination or modification of the fluid and/or undesired contamination or modification of the pressure sensing surface and wherein the presence of the flexible barrier prevents such direct contact between the fluid and the pressure sensing surface.

10. Fluid pumping apparatus comprising a fluid conduit, a pump for pumping fluid through the conduit and a system According to claim 1 for measuring the pressure of the fluid within the conduit or the pump.

11. Fluid pumping apparatus according to claim 10 wherein the pump aspirates the fluid through the conduit such that the pressure of the fluid is at least some of the time less than the ambient atmospheric pressure.

12. A method for measuring the pressure of a fluid, said method comprising the steps of:
   (A) providing a system for measuring the pressure of fluid, said system comprising i) a pressure sensing apparatus that has a pressure receiving surface and ii) a flexible barrier disposed between the pressure receiving surface and the fluid, and iii) a vacuum channel through which negative pressure may be applied to evacuating any air from between the flexible barrier and the pressure receiving surface;
   (B) applying negative pressure to the vacuum channel to evacuate any air from between the flexible barrier and the pressure receiving surface thereby causing said flexible barrier to be coupled to the pressure receiving surface such that accurate sensing of the fluid pressure will occur even if the pressure of the fluid is or becomes less than the ambient atmospheric pressure;
   (C) positioning the system such that the fluid contacts the flexible barrier but not the pressure sensing surface and the pressure of the fluid is transmitted through the flexible barrier to the pressure sensing surface, thereby causing the pressure sensing apparatus to measure the pressure of the fluid.

13. A method according to claim 12 wherein the fluid is being pumped through a pump that has a pump housing and wherein Step C comprises positioning the system such that fluid within the pump housing contacts the flexible barrier.

14. A method according to claim 12 wherein the fluid is flowing through a conduit and wherein Step C comprises positioning the system such that fluid flowing through the conduit contacts the flexible barrier.

* * * * *